(12) United States Patent
Lin et al.

(10) Patent No.: US 9,974,487 B2
(45) Date of Patent: May 22, 2018

(54) HEART RATE DETECTION MODULE, AND DETECTION AND DENOISING METHOD THEREOF

(71) Applicant: PixArt Imaging Inc., Hsin-Chu County (TW)

(72) Inventors: Chih-Hsin Lin, Hsin-Chu County (TW); Ren-Hau Gu, Hsin-Chu County (TW)

(73) Assignee: PIXART IMAGING INC., Hsin-Chu (TW)

( * ) Notice: Subject to any disclaimer, the term of this patent is extended or adjusted under 35 U.S.C. 154(b) by 380 days.

(21) Appl. No.: 14/731,711

(22) Filed: Jun. 5, 2015

(65) Prior Publication Data
US 2016/0089086 A1 Mar. 31, 2016

(30) Foreign Application Priority Data
Sep. 26, 2014 (TW) .............................. 103133698 A

(51) Int. Cl.
*A61B 5/02* (2006.01)
*A61B 5/00* (2006.01)
*A61B 5/024* (2006.01)

(52) U.S. Cl.
CPC .......... *A61B 5/721* (2013.01); *A61B 5/02416* (2013.01); *A61B 5/02438* (2013.01); *A61B 5/725* (2013.01); *A61B 5/7257* (2013.01)

(58) Field of Classification Search
CPC .......................... A61B 5/02416; A61B 5/0261
See application file for complete search history.

(56) References Cited

U.S. PATENT DOCUMENTS

| 7,072,701 B2 | 7/2006 | Chen et al. |
| 2010/0113948 A1 | 5/2010 | Yang et al. |
| 2011/0257551 A1* | 10/2011 | Banet .................. A61B 5/0816 600/534 |
| 2014/0275854 A1 | 9/2014 | Venkatraman et al. |

* cited by examiner

*Primary Examiner* — Hien Nguyen
(74) *Attorney, Agent, or Firm* — Hauptman Ham, LLP

(57) ABSTRACT

A heart rate detection module including a PPG measuring device, a motion sensor and a processing unit is provided. The PPG measuring device is configured to detect a skin surface in a detection period to output a PPG signal. The motion sensor is configured to output an acceleration signal corresponding to the detection period. The processing unit is configured to respectively convert the PPG signal and the acceleration signal to first frequency domain information and second frequency domain information, determine a denoising parameter according to a maximum spectrum peak value of the second frequency domain information to denoise the first frequency domain information, and calculate a heart rate according to a maximum spectrum peak value of the denoised first frequency domain information.

13 Claims, 8 Drawing Sheets

| second frequency domain information I2 | | first frequency domain information I1 | |
|---|---|---|---|
| second frequency index | second spectrum value | first frequency index | first spectrum value |
| 0 | 20 | 0 | 45 |
| 1 | 15 | 1 | 55 |
| 2 | 10 | 2 | 60 |
| ⋮ | ⋮ | ⋮ | ⋮ |
| 25 | 85 | 25 | 400 |
| ⋮ | ⋮ | ⋮ | ⋮ |
| 28 | 70 | 28 | 420 |
| 29 | 65 | 29 | 410 |
| 30 | 70 | 30 | 400 |
| 31 | 65 | 31 | 390 |
| 32 | 60 | 32 | 400 |
| ⋮ | ⋮ | ⋮ | ⋮ |
| 58 | 450 | 58 | 1770 |
| 59 | 455 | 59 | 1790 |
| 60 | 460 | 60 | 1800 |
| 61 | 450 | 61 | 1780 |
| 62 | 445 | 62 | 1760 |
| ⋮ | ⋮ | ⋮ | ⋮ |
| 98 | 46 | 98 | 870 |
| 99 | 48 | 99 | 890 |
| 100 | 50 | 100 | 930 |
| 101 | 46 | 101 | 920 |
| 102 | 44 | 102 | 890 |
| ⋮ | ⋮ | ⋮ | ⋮ |
| 118 | 250 | 118 | 1250 |
| 119 | 255 | 119 | 1300 |
| 120 | 260 | 120 | 1350 |
| 121 | 250 | 121 | 1320 |
| 122 | 245 | 122 | 1300 |
| ⋮ | ⋮ | ⋮ | ⋮ |
| 205 | 255 | 205 | 125 |
| ⋮ | ⋮ | ⋮ | ⋮ |
| 1023 | 1 | 1023 | 2 | denoising range 20-40 denoising range 50-70 → $P_{MAX}$ $N_{HR}$ → 930 → $P_{MAX}'$ denoising range 110-130

R1/2, half, R, double, R2

FIG. 6

| three frequency indexes of first frequency domain information I1 |||
|---|---|---|
| N1 = 58 | N2 = 73 | N3 = 117 |

| reference index of second frequency domain information I2 |
|---|
| R = 120 |

| half of reference index and double of reference index ||
|---|---|
| R1/2 = 60 | R2 = 240 |

| denoising range |||
|---|---|---|
| 55~65 | 115~125 | 235~245 |

HEART RATE DETECTION MODULE, AND DETECTION AND DENOISING METHOD THEREOF

RELATED APPLICATIONS

The present application is based on and claims priority to Taiwanese Application Number 103133698, filed Sep. 26, 2014, the disclosure of which is hereby incorporated by reference herein in its entirety.

BACKGROUND

1. Field of the Disclosure

This disclosure generally relates to a heart rate detection module and, more particularly, to a heart rate detection module with a denoising function, a detection method thereof and a denoising method thereof.

2. Description of the Related Art

Conventional pulse oximeters utilize a noninvasive method to monitor the blood oxygenation and the heart rate of a user. A conventional pulse oximeter generally emits a red light beam (wavelength of about 660 nm) and an infrared light beam (wavelength of about 910 nm) to penetrate a part of the human body and detects an intensity variation of the penetrating light based on the feature that the oxyhemoglobin and the deoxyhemoglobin have different absorptivities in particular spectrum, e.g. referring to U.S. Pat. No. 7,072,701 and entitled "Method for spectrophotometric blood oxygenation monitoring". After the intensity variations of the penetrating light of the two wavelengths, e.g. photoplethysmography signals (PPG signals) are detected, the blood oxygenation can be calculated according to an equation: Blood oxygenation=$100\% \times [HbO_2]/([HbO_2]+[Hb])$, wherein $[HbO_2]$ is an oxyhemoglobin concentration; and $[Hb]$ is a deoxyhemoglobin concentration.

Generally, the intensity variations of the penetrating light of the two wavelengths detected by a pulse oximeter will increase and decrease with heartbeats. This is because blood vessels expand and contract with the heartbeats such that the blood volume through which the light beams pass will change to accordingly change the ratio of light energy being absorbed. Therefore, a user's heart rate is calculable according to information of the continuously-varied intensity.

However, when the part of the human body being detected has a relative movement with respect to the pulse oximeter, a disturbed signal can be detected such that it is not possible to detect a correct PPG signal. Therefore, a correct heart rate may not be obtainable under a condition of a non-static state, e.g. the pulse oximeter adapted to a portable electronic device or a wearable electronic device.

SUMMARY

Accordingly, the present disclosure provides a heart rate detection module with a denoising function, a detection method thereof and a denoising method thereof.

The present disclosure provides a heart rate detection module. The heart rate detection module includes a PPG measuring device, a motion sensor and a processing unit. The PPG measuring device is configured to detect a skin surface in a detection period to output a PPG signal. The motion sensor is configured to output an acceleration signal corresponding to the detection period. The processing unit is configured to respectively convert the PPG signal and the acceleration signal to first frequency domain information and second frequency domain information, determine a denoising parameter according to a maximum spectrum peak value of the second frequency domain information to denoise the first frequency domain information, and calculate a heart rate according to a maximum spectrum peak value of the denoised first frequency domain information.

The present disclosure further provides a heart rate detection method adapted to a heart rate detection module. The heart rate detection module includes a PPG measuring device, a motion sensor and a processing unit. The heart rate detection method includes the steps of: detecting, by the PPG measuring device, a skin surface in a detection period to output a PPG signal; outputting, by the motion sensor, an acceleration signal corresponding to the detection period; receiving, by the processing unit, the PPG signal and the acceleration signal; respectively converting the PPG signal and the acceleration signal to first frequency domain information and second frequency domain information; determining a denoising parameter according to a maximum spectrum peak value of the second frequency domain information to denoise the first frequency domain information; and calculating a heart rate according to a maximum spectrum peak value of the denoised first frequency domain information.

The present disclosure further provides a denoising method of a heart rate detection module. The denoising method includes the steps of: receiving a PPG signal and an acceleration signal in a detection period; converting the PPG signal to a frequency domain PPG signal and generating first frequency domain information containing a first frequency index set and a first spectrum value set associated therewith; converting the acceleration signal to a frequency domain acceleration signal and generating second frequency domain information containing a second frequency index set and a second spectrum value set associated therewith; identifying three frequency indexes corresponding to top three spectrum peak values in the first frequency domain information and a reference index corresponding to a maximum spectrum peak value in the second frequency domain information; and denoising the first spectrum value set according to the three frequency indexes and the reference index.

BRIEF DESCRIPTION OF THE DRAWINGS

Other objects, advantages, and novel features of the present disclosure will become more apparent from the following detailed description when taken in conjunction with the accompanying drawings.

FIG. 6 is a schematic diagram of first frequency domain information and second frequency domain information according to one embodiment of the present disclosure.

FIG. 8 is a schematic diagram of frequency indexes, a reference index and a denoising range according to one embodiment of the present disclosure.

DETAILED DESCRIPTION OF THE EMBODIMENT

It should be noted that, wherever possible, the same reference numbers will be used throughout the drawings to refer to the same or like parts.

The present disclosure provides a heart rate detection module with a denoising function and adaptable to a smart watch, a wristband, glasses, a wearable device or a portable device, but not limited thereto. In some embodiments, the wearable device or the portable device may or may not have a display function. In some embodiments, the heart rate detection module is an individual detection device and is attached to the devices in an appropriate manner while being used so as to improve the usability thereof.

Figure 1:
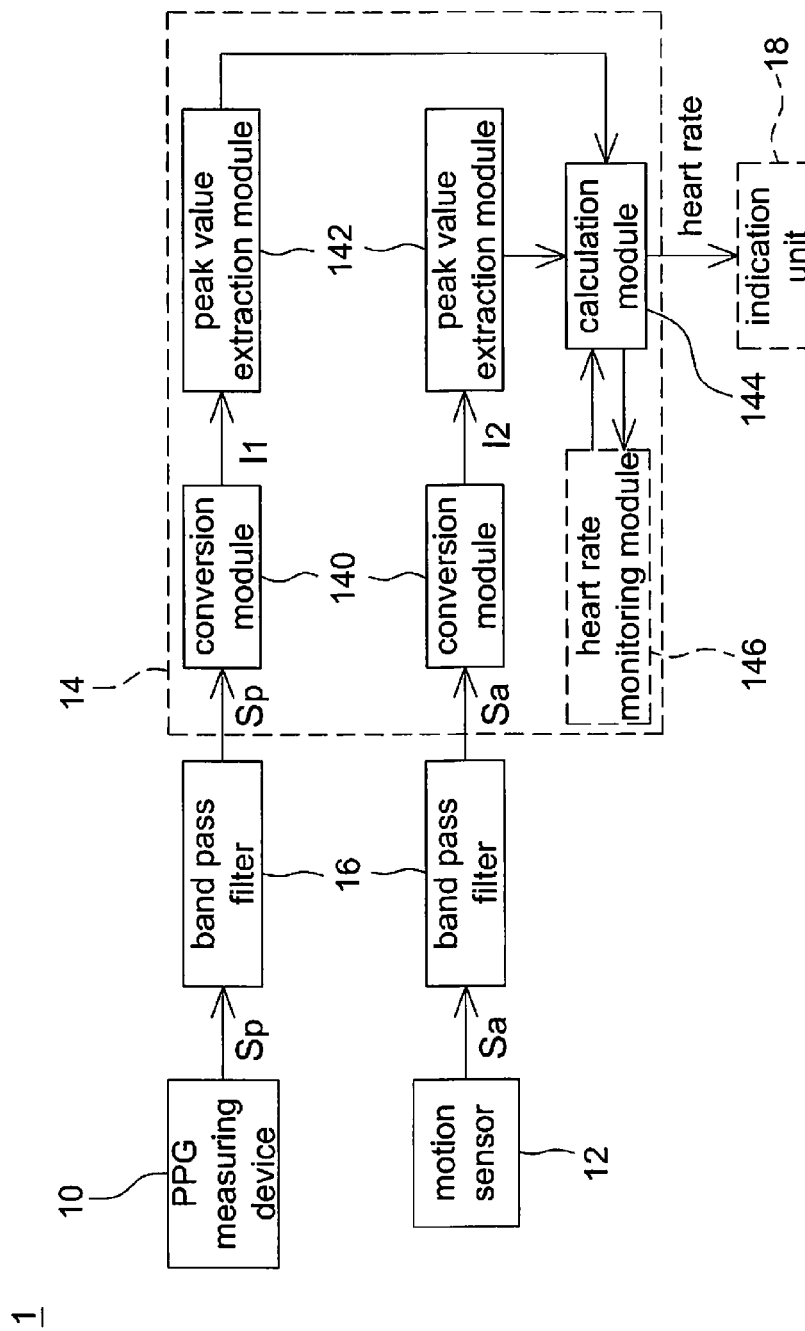
FIG. 1 is a schematic block diagram of a heart rate detection module according to one embodiment of the present disclosure.

Referring to FIG. 1, it is a schematic block diagram of a heart rate detection module 1 according to one embodiment of the present disclosure. The heart rate detection module 1 includes a photoplethysmography (PPG) measuring device 10, a motion sensor 12 and a processing unit 14, wherein the processing unit 14 includes a conversion module 140, a peak value extraction module 142 and a calculation module 144. In some embodiments, two band pass filters 16 are respectively disposed between the PPG measuring device 10 and the processing unit 14 and between the motion sensor 12 and the processing unit 14. In some embodiments, the processing unit 14 further includes a heart rate monitoring module 146 configured to record heart rates calculated by the calculation module 144. It is appreciated that a power module (not shown) is electrically connected to the heart rate detection module 1 for providing power required by the heart rate detection module 1 in operation.

The PPG measuring device 10 is configured to detect a skin surface in a detection period to output a PPG signal $S_p$. Generally speaking, the PPG measuring device 10 has a light emitting module and a sensing region. The PPG measuring device 10 is a reflective PPG measuring device or a transmissive PPG measuring device without particularly limitations. The method for the PPG measuring device 10 to generate the PPG signal $S_p$ according to detected light signals is known to the art and thus details thereof are not described herein. A location of the skin surface to be detected by the PPG measuring device 10 is not particularly limited and is determined according to an electronic device to which the heart rate detection module 1 adapted.

The motion sensor 12 is, for example, a gyroscope, an accelerometer, a G sensor or other devices configured to sense human body movement. In this embodiment, the motion sensor 12 is illustrated by taking an accelerometer as an example. The motion sensor 12 is configured to output an acceleration signal $S_a$ corresponding to the detection period of the PPG measuring device 10 so that the acceleration signal $S_a$ has a corresponding relationship with the PPG signal $S_p$. In one embodiment, the motion sensor 12 is manufactured by micro-electro-mechanical systems (MEMS) technology.

Figure 2A:
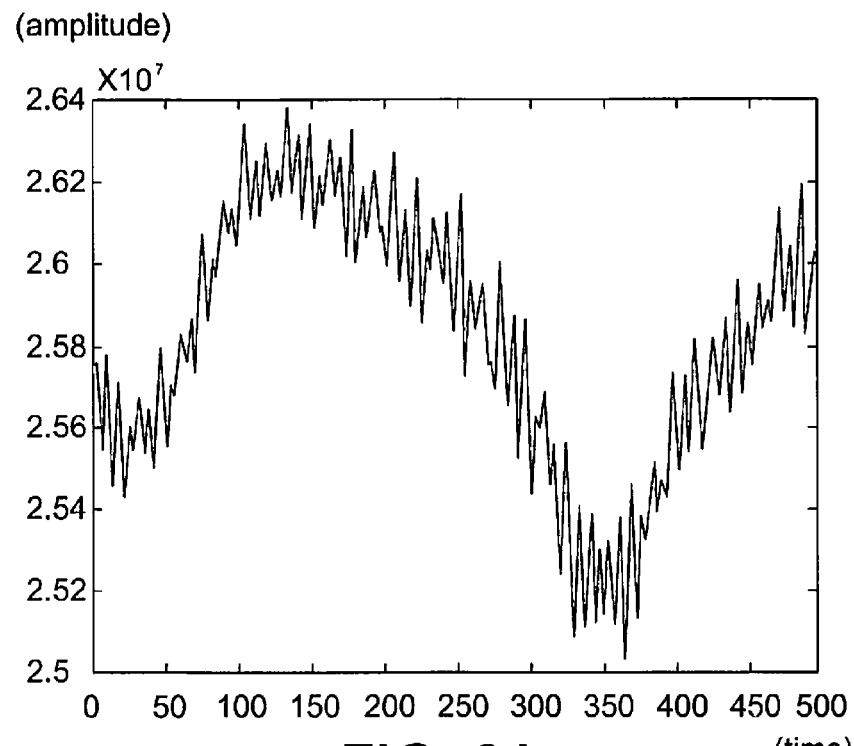
FIG. 2A is a schematic diagram of a PPG signal before being filtered according to one embodiment of the present disclosure.
Figure 2B:
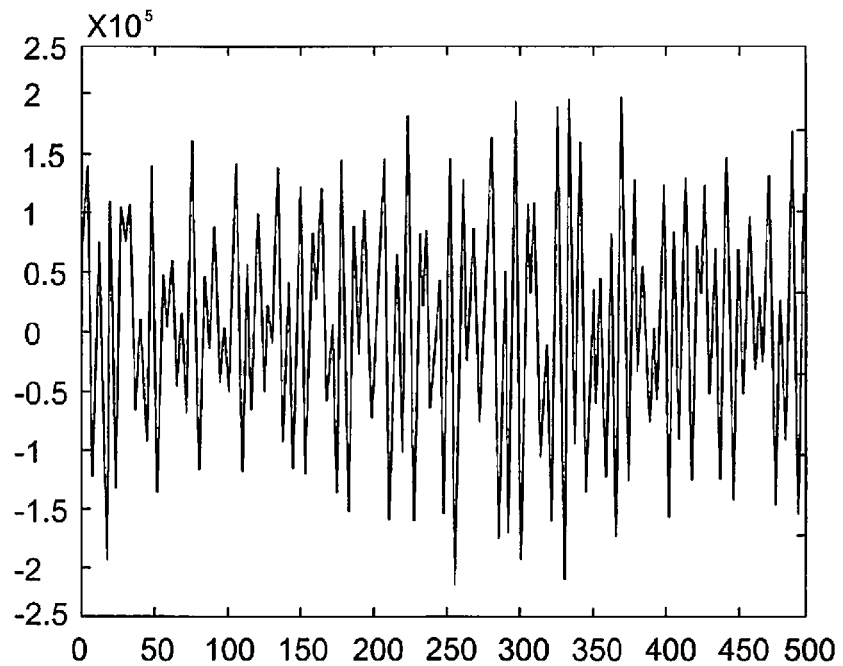
FIG. 2B is a schematic diagram of a PPG signal after being filtered according to one embodiment of the present disclosure.

In this embodiment, the heart rate detection module 1 has two band pass filters 16 respectively between the PPG measuring device 10 and the processing unit 14 and between the motion sensor 12 and the processing unit 14, and the two band pass filters 16 are respectively configured to filter the PPG signal $S_p$ and the acceleration signal $S_a$. For example, FIGS. 2A and 2B are schematic diagrams of the PPG signal $S_p$ before and after being filtered by the band pass filter 16, wherein the x-axis indicates the time and the y-axis indicates the amplitude. Generally speaking, a human heart rate is between 30 beats/min and 240 beats/min, and a signal frequency range of the human heart rate is from 0.5 Hz to 4 Hz since a heart rate of 60 beats/min corresponds to 1 Hz. Therefore, a passband of the band pass filters 16 is selected, for example, from 0.5 Hz to 4 Hz or from 0.45 Hz to 4.5 Hz so as to improve the signal quality of the PPG signal $S_p$ and the acceleration signal $S_a$ (i.e. filtering frequencies not related to the human heart rate), but not limited thereto. To simplify the description, the PPG signal and the acceleration signal after being filtered by the band pass filters 16 are also indicated by reference numbers $S_p$ and $S_a$, respectively.

It should be mentioned that although the band pass filters 16 are not included in the processing unit 14 in FIG. 1, the present disclosure is not limited thereto. In some embodiments, the band pass filters 16 are respectively disposed in the PPG measuring device 10 and the motion sensor 12. In some embodiments, the band pass filters 16 are disposed in the processing unit 14.

The processing unit 14 is, for example, a digital signal processor (DSP) or other processing devices for processing signals, and processing functions thereof are implemented by software, hardware or firmware. The processing unit 14 is configured to eliminate, according to the acceleration signal $S_a$, noise in the PPG signal $S_p$ generated by relative movements between the sensing region of the PPG measuring device 10 and the skin surface. For example, in some embodiments, the processing unit 14 converts the PPG signal $S_p$ and the acceleration signal $S_a$ respectively to first frequency domain information $I_1$ and second frequency domain information $I_2$, determines a denoising parameter according to a maximum spectrum peak value of the second frequency domain information $I_2$ to denoise the first frequency domain information $I_1$, and calculates a heart rate according to a maximum spectrum peak value of the denoised first frequency domain information.

The conversion module 140 of the processing unit 14 is configured to convert the PPG signal $S_p$ to a frequency domain PPG signal, generate a first frequency index set and a first spectrum value set associated with the first frequency index set configured as the first frequency domain information $I_1$, convert the acceleration signal $S_a$ to a frequency domain acceleration signal, and generate a second frequency index set and a second spectrum value set associated with the second frequency index set configured as the second frequency domain information $I_2$.

The peak value extraction module 142 of the processing unit 14 is configured to identify a plurality of spectrum peak values in the first frequency domain information $I_1$ and the second frequency domain information $I_2$, and output frequency indexes corresponding to the plurality of spectrum peak values to the calculation module 144.

The calculation module 144 of the processing unit 14 is configured to eliminate noise in the first frequency domain information $I_1$ according to the frequency indexes corresponding to the plurality of spectrum peak values and then calculate the heart rate (described later).

The heart rate monitoring module 146 is configured to record a variation tendency of heart rates corresponding to a plurality of the detection periods so that when the calculation module 144 is unable to directly calculate a heart rate according to the denoised first frequency domain information, the heart rate is further estimated according the variation tendency (described later).

It is appreciated that the conversion module 140, the peak value extraction module 142, the calculation module 144 and the heart rate monitoring module 146 of this embodiment indicate function blocks or program instructions inside the processing unit 14. It is appreciated that in other embodiments, the conversion module 140, the peak value extraction module 142, the calculation module 144 and the heart rate monitoring module 146 may be implemented by different processing units. It should be mentioned that two conversion modules 140 and two peak value extraction modules 142 are shown in FIG. 1, but the present disclosure is not limited thereto. The processing unit 14 may include only one conversion module 140 and only one peak value extraction module 142.

In some embodiments, the heart rate detection module 1 further includes an indication unit 18, e.g. a speaker or a display, configured to represent the heart rate through audio or images. In this case, the power module further provides power required by the indication unit 18.

In some embodiments, the indication unit 18 is not included in the heart rate detection module 1. For example, when the heart rate detection module 1 is integrated with a smart band, the indication unit 18 may be a display screen of a smart phone. In this case, the heart rate detection module 1 transmits a signal containing the heart rate information from the smart band to the smart phone in a wireless manner (e.g. Bluetooth, Wi-Fi, ZigBee or other wireless communication protocols) to show the heart rate and the variation tendency thereof in real time.

In some embodiments, the indication unit 18 is disposed in a computer system connected to a cloud system. In this case, the heart rate detection module 1 transmits a signal containing the heart rate information to the cloud system in a wireless manner for the cloud system to record the heart rate. In therapeutic applications, a medical staff may monitor the user's heart rate through the computer system.

It is appreciated that the heart rate detected by the heart rate detection module 1 may be used for different applications. In the present disclosure, it is to eliminate signal noise in the PPG signal by using the acceleration signal so as to improve the accuracy of calculating the heart rate.

Figure 3:
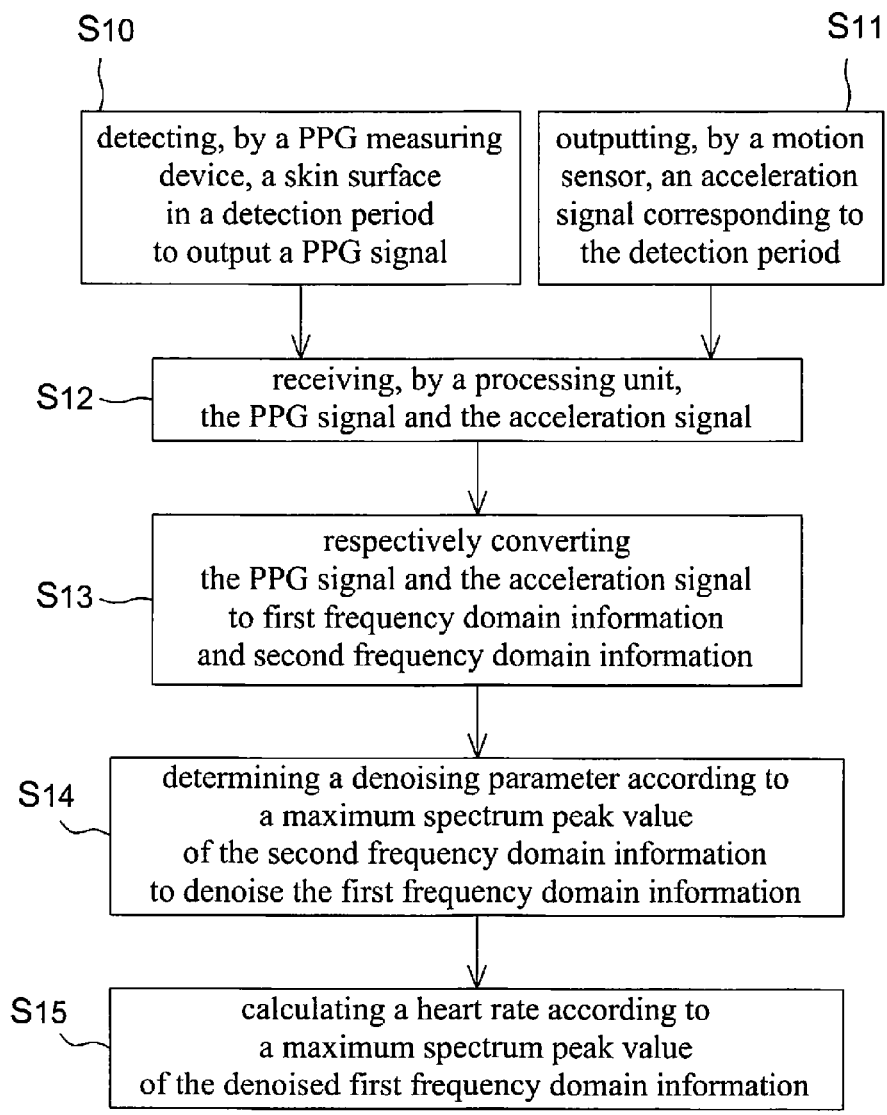
FIG. 3 is a flow chart of a heart rate detection method according to one embodiment of the present disclosure.

FIG. 3 is a flow chart of a heart rate detection method according to one embodiment of the present disclosure. The heart rate detection method includes the steps of: detecting, by a PPG measuring device, a skin surface in a detection period to output a PPG signal (Step $S_{10}$); outputting, by a motion sensor, an acceleration signal corresponding to the detection period (Step $S_{11}$); receiving, by a processing unit, the PPG signal and the acceleration signal (Step $S_{12}$); respectively converting the PPG signal and the acceleration signal to first frequency domain information and second frequency domain information (Step $S_{13}$); determining a denoising parameter according to a maximum spectrum peak value of the second frequency domain information to denoise the first frequency domain information (Step $S_{14}$); and calculating a heart rate according to a maximum spectrum peak value of the denoised first frequency domain information (Step $S_{15}$).

Figures 4A, 4B:
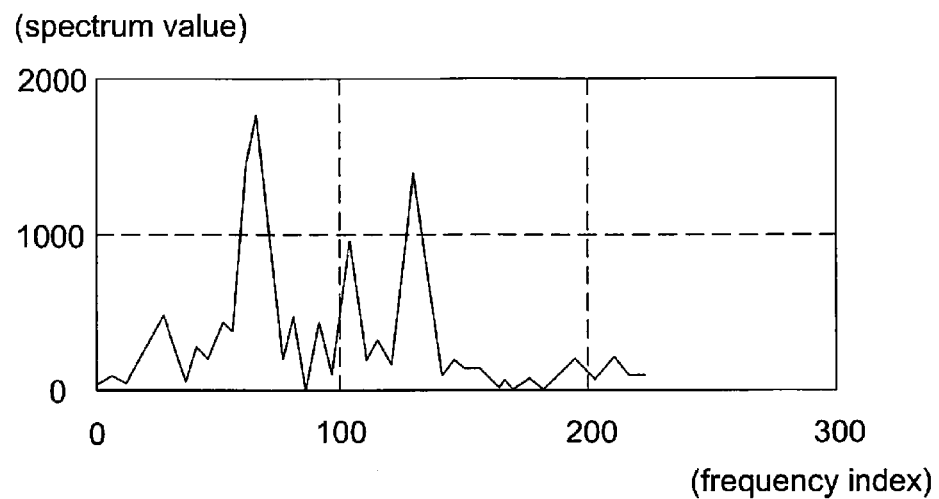
FIG. 4A is a spectrum diagram of a frequency domain PPG signal according to one embodiment of the present disclosure.
FIG. 4B is a schematic diagram of first frequency domain information corresponding to the spectrum diagram of FIG. 4A.
Figures 5A, 5B:
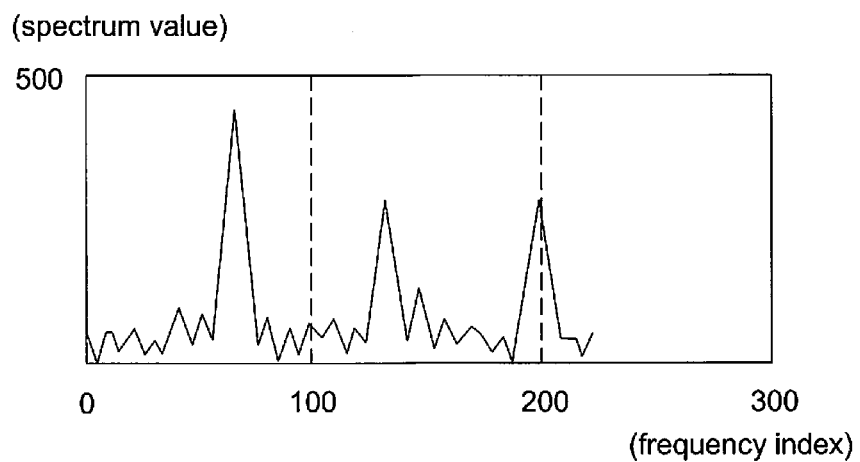
FIG. 5A is a spectrum diagram of a frequency domain acceleration signal according to one embodiment of the present disclosure.
FIG. 5B is a schematic diagram of second frequency domain information corresponding to the spectrum diagram of FIG. 5A.

Referring to FIGS. 1, 3, 4A, 4B, 5A, 5B and 6 together, details of this embodiment are described hereinafter, wherein FIGS. 4A and 4B are respectively a spectrum diagram of a frequency domain PPG signal and a schematic diagram of first frequency domain information according to one embodiment of the present disclosure, FIGS. 5A and 5B are respectively a spectrum diagram of a frequency domain acceleration signal and a schematic diagram of second frequency domain information according to one embodiment of the present disclosure, and FIG. 6 is a schematic diagram of the first frequency domain information and the second frequency domain information according to one embodiment of the present disclosure. It is appreciated that FIGS. 4A, 4B, 5A, 5B and 6 are only intended to illustrate, but not to limit the present disclosure.

Step $S_{10}$ to $S_{11}$: Firstly, a PPG measuring device 10 of a heart rate detection module 1 detects a skin surface in a detection period to output a PPG signal $S_p$. Meanwhile, a motion sensor 12 outputs an acceleration signal $S_a$ corresponding to the detection period. To simplify the description, the PPG signal $S_p$ and the acceleration signal $S_a$ in the following descriptions may indicate signals filtered by the band pass filters 16 without further indications. It should be mentioned that since the acceleration signal $S_a$ is mainly used to eliminate noise in the PPG signal $S_p$ generated by relative movements between a sensing region of the PPG measuring device 10 and the skin surface, preferably the PPG signal $S_p$ and the acceleration signal $S_a$ are related to substantially identical detection periods so that the heart rate detection module 1 may denoise information related to the PPG signal $S_p$ according to information related to the acceleration signal $S_a$ in calculating the heart rate.

Step $S_{12}$: Then, the processing unit 14 receives the PPG signal $S_p$ and the acceleration signal $S_a$ together for post processing. As shown in FIG. 1, the PPG signal $S_p$ and the acceleration signal $S_a$ are respectively inputted to a conversion module 140 of the processing unit 14.

Step $S_{13}$: The conversion module 140 of the processing unit 14 converts the PPG signal $S_p$ to a frequency domain PPG signal and generate a first frequency index set and a first spectrum value set associated with the first frequency index set, wherein each frequency index corresponds to one spectrum value. It should be mentioned that the conversion module 140 of this embodiment may use Fast Fourier Transform (FFT) to convert the PPG signal $S_p$ from time domain to frequency domain to generate the frequency domain PPG signal, but the present disclosure is not limited thereto. In other embodiments, the conversion module 140 may use Discrete Fourier Transform (DFT) or other time domain to frequency domain conversion methods (i.e. spectrum analysis) to convert the PPG signal $S_p$.

It should be mentioned that the frequency domain PPG signal is a discrete signal so that the processing unit 14 is able to perform digital signal processing accordingly. In some embodiments, when the PPG signal $S_p$ outputted by the PPG measuring device 10 is a continuous time domain signal, the conversion module 140 firstly converts the PPG signal $S_p$ to a discrete time domain signal (e.g. by sampling the PPG signal $S_p$ with a sampling frequency), and then converts the discrete time domain signal to a discrete frequency domain signal accordingly, but not limited thereto. In other embodiments, the conversion module 140 firstly converts the PPG signal $S_p$ to a continuous frequency domain signal, and then converts the continuous frequency domain signal to a discrete frequency domain signal accordingly.

As mentioned above, a signal frequency range of the human heart rate is from 0.5 Hz to 4 Hz. It is assumed that a maximum value of the signal frequency of the human heart rate is 4 Hz (corresponding to 240 beats/min), and a sampling frequency has to be larger than 8 Hz (e.g. 10 Hz or 20 Hz) so that Nyquist theorem is satisfied. In one embodiment in using FFT, the sampling frequency is 20 Hz, but not limited thereto. The sampling frequency is determined according to operating capability of the processing unit 14.

After the conversion module 140 uses FFT to convert the PPG signal $S_p$ to the frequency domain PPG signal, a spectrum diagram corresponding to the frequency domain PPG signal is generated, as shown in FIG. 4A, wherein the x-axis of the spectrum diagram indicates the frequency index of FFT and the y-axis indicates the spectrum amplitude. In this embodiment, frequency indexes and spectrum amplitudes corresponding to the frequency indexes in FIG. 4A are respectively configured as a first frequency index set and a first spectrum value set associated with the first frequency index set, i.e. first frequency domain information $I_1$, as shown in FIG. 4B.

It should be mentioned that a number of the frequency indexes of FFT is, for example, 1024 bins, but not limited thereto, wherein each of the frequency indexes corresponds to one frequency. For example, a frequency corresponding to a frequency index 256 is (20 Hz/1024)×256=5 Hz. It is appreciated that when the sampling frequency is 20 Hz and the number of the frequency indexes is 1024 bins, a frequency resolution of the first frequency domain information $I_1$ is about 20 Hz/1024=0.0195 Hz. When the sampling frequency is a fixed value and the number of the frequency indexes is higher, a frequency difference between two adjacent frequency indexes becomes smaller so that the heart rate detection module 1 has a higher sensitivity in calculating the heart rate according to the frequency indexes.

It should be mentioned that since the human heart rate is between 30 beats/min and 240 beats/min, a frequency index range corresponding to the human heart rate in the first frequency domain information $I_1$ is substantially from 25 to 205. Therefore, in some embodiments, the processing unit 14 removes (or releases) frequency indexes smaller than 25 and/or larger than 205 and the associated spectrum values for saving system resources, but not limited thereto.

Similarly, another conversion module 140 in the processing unit 14 uses the same way as converting the PPG signal $S_p$ to convert the acceleration signal $S_a$ to generate a spectrum diagram corresponding to the frequency domain acceleration signal, as shown in FIG. 5A, and generate a second frequency index set and a second spectrum value set associated with the second frequency index set configured as second frequency domain information $I_2$, as shown in FIG. 5B. In some embodiments, in the second frequency domain information $I_2$, only frequency indexes within the frequency index range (e.g. from 25 to 205) and the associated spectrum values are reserved.

Step $S_{14}$: After the second frequency domain information $I_2$ is obtained, the peak value extraction module 142 determines a reference index R according to a frequency index corresponding to a maximum spectrum peak value $P_{MAX}$ in the second frequency domain information $I_2$. For example, referring to FIG. 6, it is assumed that a maximum spectrum peak value is 460 in the second frequency domain information $I_2$. In this case, the peak value extraction module 142 identifies that the maximum spectrum peak value $P_{MAX}$ is 460 and outputs a frequency index 60 corresponding to the maximum spectrum peak value $P_{MAX}$ to the calculation module 144 configured as the reference index R. Then, the calculation module 144 calculates a half of the reference index R and a double of the reference index R. For example, when the reference index R is 60, the half of reference index $R_{1/2}$ is 30 and the double of reference index $R_2$ is 120. It is appreciated that since each of the frequency indexes indicates one frequency, a frequency corresponding to the double of reference index $R_2$ is a double of the frequency corresponding to the reference index R, and a frequency corresponding to the half of reference index $R_{1/2}$ is a half of the frequency corresponding to the reference index R.

Meanwhile, the calculation module 144 determines a denoising parameter according to the reference index R and at least one of the half of reference index $R_{1/2}$ and the double of reference index $R_2$ to denoise the first spectrum value set. For example, the denoising parameter may contain the reference index R and the half of reference index $R_{1/2}$, contain the reference index R and the double of reference index $R_2$, or contain the reference index R, the half of reference index $R_{1/2}$ and the double of reference index $R_2$. Denoising the first spectrum value set is referred to remove spectrum values in the first frequency domain information $I_1$ corresponding to the reference indexes and nearby reference indexes according to the denoising parameter obtained by the reference index R. For example, when the reference indexes $R_{1/2}$, R and $R_2$ are 30, 60 and 120 respectively, the processing unit 14 may determine, by respectively plus and minus a predetermined range to and from the reference indexes, a denoising range as 20 to 40, 50 to 70 and 110 to 130 (i.e. 30±10, 60±10 and 120±10), and remove spectrum values in the first spectrum value set associated with the denoising range configured as a method to denoise the first frequency domain information $I_1$. In some embodiments, the predetermined range is set before the shipment of the heart rate detection module 1 or in the initialization of the heart rate detection module 1.

In addition, since the second frequency domain information $I_2$ is configured for the processing unit 14 to determine the denoising parameter, in some embodiments, the processing unit 14 removes (or releases) the second frequency domain information $I_2$ for saving system resources after the calculation module 144 obtains the maximum spectrum peak value $P_{MAX}$ from the peak value extraction module 142 or after the denoising parameter is determined, but not limited thereto.

Step $S_{15}$: Finally, the calculation module 144 calculates a heart rate according to a maximum spectrum peak value of the denoised first frequency domain information. More specifically speaking, when the maximum spectrum peak value in the first frequency domain information $I_1$ is identified, the calculation module 144 removes spectrum values corresponding to the denoising range (i.e. spectrum values in the first frequency index set corresponding to the frequency indexes 20 to 40, 50 to 70 and 110 to 130). For example, after spectrum values corresponding to the denoising range are removed according to the embodiment of FIG. 6 (e.g. areas with oblique lines indicating the range of the spectrum values to be removed), the maximum spectrum peak value of the denoised first frequency domain information is determined as 930 (i.e. a denoised maximum spectrum peak value $P_{MAX}'$). The calculation module 144 then calculates a heart rate according to a frequency index (i.e. 100) corresponding to the denoised maximum spectrum peak value $P_{MAX}'$. As mentioned above, the heart rate is (20/1024)×100×60=117.19 beats/min since a heart rate of 60 beats/min corresponds to 1 Hz. Accordingly, even if the PPG measuring device 10 outputs a PPG signal containing disturbed waveform in a non-static state, the heart rate detection module 1 is still able to calculate an accurate heart rate according to the above steps.

It should be mentioned that in this embodiment, the calculation module 144 only removes (or ignores) spectrum values in the first frequency domain information $I_1$ corresponding to the denoising parameter but not to directly delete the spectrum values from a memory in identifying the maximum spectrum peak value of the first frequency domain information $I_1$ (e.g. in calculating the heart rate), but the present disclosure is not limited thereto. In some embodiments, before the step $S_{15}$ or after the denoising parameter is determined, the processing unit 14 may remove frequency indexes and spectrum values in the first frequency domain information $I_1$ corresponding to the denoising parameter from the memory in advance for saving system resources.

On the other hand, to improve the accuracy of calculating the heart rate, in some embodiments, the processing unit 14 takes a frequency index corresponding to the maximum spectrum peak value (e.g. $P_{MAX}'$) of the denoised first frequency domain information as a heart rate index $N_{HR}$ (e.g. 100). Then, a heart rate is calculated according to the heart rate index $N_{HR}$ and frequency indexes adjacent to the heart rate index $N_{HR}$. For example, referring to FIG. 6 again, when the heart rate index $N_{HR}$ is 100, the heart rate detection module 1 calculates an energy center as (99×890+100×930+ 101×920)/(890+930+920)=100.011 according to the heart rate index $N_{HR}$, two frequency indexes 99 and 101 adjacent to the heart rate index $N_{HR}$, and spectrum values 930, 890 and 920 respectively corresponding thereto. Then, the calculation module 144 calculates the heart rate as (20/1024)× 100.011×60=117.20 beats/min according to the energy center, but not limited thereto. The calculation module 144 may calculate the heart rate according to the heart rate index and a plurality of frequency indexes (e.g. 4 or 6 frequency indexes) adjacent to the heart rate index.

Since the heart rate detection module 1 calculates one heart rate in each detection period, the heart rate detection module 1 may calculate, according to heart rates of a plurality of detection periods, a variation tendency of the heart rates of the plurality of detection periods to estimate a heart rate accordingly. In some embodiments, the processing unit 14 further includes a heart rate monitoring module 146 configured to record a variation tendency of the heart rates corresponding to a plurality of the detection periods. For example, in the embodiment of FIG. 6, after a user exercises for a period (wherein the period is, for example, longer than at least twice of the detection period), it is assumed that the denoising range is not changed and the heart rate index $N_{HR}$ varies from 100 to 110. As the calculation module 144 may ignore spectrum values corresponding to the denoising range (i.e. spectrum values corresponding to the frequency indexes 110 to 130 in the first frequency index set) when identifying the maximum spectrum peak value in the first frequency domain information $I_1$, the heart rate index $N_{HR}$ will be ignored in this case, and the calculation module 144 further estimates a current heart rate according to the variation tendency (e.g. a tendency that the heart rate index $N_{HR}$ varies from 100 to 110 during the period) recorded by the heart rate monitoring module 146.

In one aspect according to the embodiment of FIG. 6, when the heart rate index $N_{HR}$ gradually varies from 100 to 110, the calculation module 144 partially ignores spectrum values corresponding to the denoising range, e.g. ignoring spectrum values corresponding to the frequency indexes 20 to 40 and 50 to 70 but not ignoring spectrum values corresponding to the frequency indexes 110 to 130 in the first frequency index set. That is to say, the calculation module 144 takes the denoising range 110 to 130 as an invalid denoising range according to a variation of the heart rate index $N_{HR}$. In this case, the calculation module 144 calculates the heart rate according to the heart rate index $N_{HR}$ or a maximum spectrum peak value of the denoised first frequency domain information (e.g. a frequency index 120 corresponding to the spectrum value 1350 in the first spectrum value set).

Figure 7:
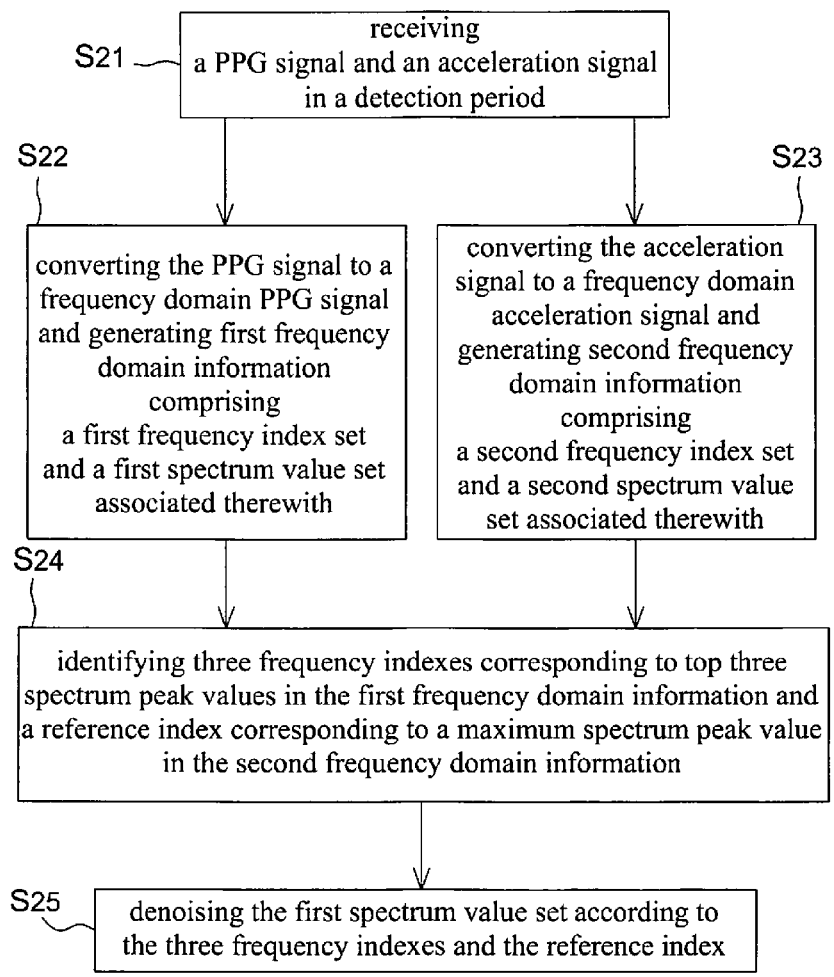
FIG. 7 is a flow chart of a denoising method according to one embodiment of the present disclosure.

FIG. 7 is a flow chart of a denoising method according to one embodiment of the present disclosure. The denoising method includes the steps of: receiving a PPG signal and an acceleration signal in a detection period (Step $S_{21}$); converting the PPG signal to a frequency domain PPG signal and generating first frequency domain information containing a first frequency index set and a first spectrum value set associated therewith (Step $S_{22}$); converting the acceleration signal to a frequency domain acceleration signal and generating second frequency domain information containing a second frequency index set and a second spectrum value set associated therewith (Step $S_{23}$); identifying three frequency indexes corresponding to top three spectrum peak values in the first frequency domain information and a reference index corresponding to a maximum spectrum peak value in the second frequency domain information (Step $S_{24}$); and denoising the first spectrum value set according to the three frequency indexes and the reference index (Step $S_{25}$).

Referring to FIGS. 1, 6, 7 and 8 together, details of this embodiment are described hereinafter, wherein FIG. 8 is a schematic diagram of frequency indexes, a reference index and a denoising range according to one embodiment of the present disclosure.

Step $S_{21}$: Firstly, a PPG signal $S_p$ and an acceleration signal $S_a$ are received in a detection period. It is appreciated that the PPG signal $S_p$ and the acceleration signal $S_a$ are, for example, respectively outputted from a PPG measuring device 10 and a motion sensor 12, as shown in FIG. 1.

Step $S_{22}$: Then, the PPG signal $S_p$ is converted to a frequency domain PPG signal by using FFT or other time domain to frequency domain conversion methods, and first frequency domain information $I_1$ containing a first frequency index set and a first spectrum value set associated with the first frequency index set is generated, as shown in FIG. 6.

Step $S_{23}$: The acceleration signal $S_a$ is converted to a frequency domain acceleration signal by using the same method as converting the PPG signal $S_p$, and second frequency domain information $I_2$ containing a second frequency index set and a second spectrum value set associated with the second frequency index set is generated. In this embodiment, since the heart rate detection module 1 includes two independent conversion modules 140, the steps $S_{23}$ and $S_{22}$ may be performed at the same time, but not limited thereto.

It is appreciated that a processing unit 14 may reserve required information of frequency indexes and spectrum values in the first frequency domain information $I_1$ and the second frequency domain information $I_2$ and store in a memory unit, e.g. only reserving the frequency indexes 0 to 225 and spectrum values associated therewith, but not limited thereto.

Step $S_{24}$: After the first frequency domain information $I_1$ and the second frequency domain information $I_2$ are obtained, the processing unit 14 identifies three frequency indexes $N_1$, $N_2$ and $N_3$ corresponding to top three spectrum peak values in the first frequency domain information $I_1$ and a reference index R corresponding to a maximum spectrum peak value in the second frequency domain information $I_2$. For example, the three frequency indexes $N_1$, $N_2$ and $N_3$ corresponding to the top three spectrum peak values in the first frequency domain information $I_1$ are respectively 58, 73 and 117, and the reference index R corresponding to the maximum spectrum peak value in the second frequency domain information $I_2$ is 120, as shown in FIG. 8.

Step $S_{25}$: Finally, the processing unit 14 calculates a half of frequency index $R_{1/2}$ and/or a double of frequency index $R_2$ as 60 and 240, and determines a denoising range, wherein the denoising range is, for example, determined by plus and minus 5 to and from the reference indexes $R_{1/2}$, R and $R_2$, as 55 to 65, 115 to 125 and 235 to 245, as shown in FIG. 8. Accordingly, the processing unit 14 denoises the frequency domain PPG signal according to the denoising range determined by the three frequency indexes $N_1$ to $N_3$ and the reference index R.

As mentioned above, in a non-static state, the PPG measuring device 10 may output incorrect PPG signals so that the processing unit 14 may not directly calculate a correct heart rate according to the PPG signal. Therefore, after the denoising range is determined through the steps $S_{21}$ to $S_{25}$ of this embodiment, spectrum values in the first frequency domain information $I_1$ associated with frequency indexes within the denoising range may be noise, and the processing unit 14 may remove frequency indexes in the first frequency domain information $I_1$ within the denoising range or spectrum values associated with the frequency indexes so as to denoise the first frequency domain information $I_1$.

In one application, the denoising method is adapted to, for example, calculate a heart rate. Referring to FIG. 8 again, when the frequency indexes $N_1$ and $N_3$ of the first frequency domain information $I_1$ is in the denoising range (i.e. 58 and 117 are respectively between 55 to 65 and 115 to 125) and the frequency index $N_2$ is not in the denoising range, the processing unit 14 may determine a heart rate index $N_{HR}$ as 73 (i.e. the frequency index $N_2$) among the three frequency indexes $N_1$, $N_2$ and $N_3$ according to the denoising range. Then, the processing unit 14 calculates a heart rate according to the heart rate index $N_{HR}$. For example, the heart rate is $(20/1024) \times 73 \times 60 = 85.55$ beats/min. In some embodiment, the processing unit 14 calculates a heart rate according to the heart rate index $N_{HR}$ and frequency indexes adjacent to the heart rate index $N_{HR}$. The calculation method thereof is described above and thus details thereof are not repeated herein.

It should be mentioned that the denoising range is based on the frequency indexes $N_1$ to $N_3$ and generated by plus and minus a predetermined range (i.e. 5) to and from the frequency indexes $N_1$ to $N_3$, wherein the predetermined range may or may not be related to a sampling frequency of the conversion module 140 and a number of the frequency indexes. As mentioned above, a frequency resolution is determined by the sampling frequency and the number of the frequency indexes. In some embodiments, the predetermined range is inversely correlated with the frequency resolution, but not limited thereto.

In some embodiments, the processing unit 14 further determines two residual indexes as 58 and 117 (i.e. the frequency indexes $N_1$ and $N_3$) among the three frequency indexes $N_1$ to $N_3$ according to the denoising range. It is assumed that the denoising range and the residual indexes $N_1$ and $N_3$ are not changed. After a user exercises for a period, since the user's heart rate rises, the frequency index $N_2$ associated with the heart rate is gradually approaching the frequency index $N_3$ so that the frequency index $N_2$ falls into the denoising range (i.e. the frequency indexes 115 to 125). In this case, the processing unit 14 may not determine the heart rate index $N_{HR}$ among the three frequency indexes $N_1$ to $N_3$ according to the denoising range. Therefore, when a difference value between the heart rate index $N_{HR}$ (e.g. the frequency index $N_2$) and one of the residual indexes (e.g. the frequency indexes $N_1$ or $N_3$) is smaller than a threshold, the processing unit 14 may estimate a heart rate according to a variation tendency of the heart rate indexes $N_{HR}$ corresponding to a plurality of the detection periods.

For example, it is assumed that the threshold is 10 and the heart rate index $N_{HR}$ varies from 73 to 110 after the period. In this case, a difference value between the heart rate index $N_{HR}$ and the residual index 117 (i.e. the frequency index $N_3$) is 7, which is smaller than the threshold, and the processing unit 14 then estimates a heart rate according to the variation tendency of the heart rate indexes $N_{HR}$ corresponding to a plurality of the detection periods, wherein the heart rate calculation method according to the variation tendency and the frequency indexes is described above, and thus details thereof are not repeated herein.

In the above embodiments, the PPG signal $S_p$ of the PPG measuring device 10 and the acceleration signal $S_a$ of the motion sensor 12 are not only configured to calculate a heart rate. The processing unit 14 further calculates a physiology state and exercise data (e.g. step counting, running/riding velocity calculation, and sport time recording) according to the PPG signal $S_p$ and the acceleration signal $S_a$ according to different applications.

As mentioned above, the conventional pulse oximeter of the heart rate detection module generates incorrect PPG signals when calculating a heart rate under a condition of a non-static state thereby decreasing the calculation accuracy of the heart rate. Therefore, the present disclosure further provides a heart rate detection module with a denoising function (e.g. FIG. 1), a detection method thereof (e.g. FIG. 2) and a denoising method thereof (e.g. FIG. 7) that may determine a denoising parameter through an acceleration signal to eliminate noise in a PPG signal so that the calculation accuracy of the heart rate is increased.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A heart rate detection module, comprising:
   a PPG measuring device configured to detect a skin surface in a detection period to output a PPG signal;
   a motion sensor configured to output an acceleration signal corresponding to the detection period;
   a band pass filter configured to filter the PPG signal and the acceleration signal; and
   a processing unit comprising a conversion module, a peak value extraction module and a calculation module,
   the conversion module configured to respectively convert the PPG signal and the acceleration signal to
      first frequency domain information, which comprises a first frequency index set and a first spectrum value set associated with the first frequency index set, and
      second frequency domain information, which comprises a second frequency index set and a second spectrum value set associated with the second frequency index set,
   the peak value extraction module configured to identify a plurality of frequency indexes corresponding to a plurality of spectrum peak values in the first frequency domain information and the second frequency domain information, the calculation module configured to determine a reference index as a denoising parameter according to a frequency index corresponding to a maximum spectrum peak value of the second frequency domain information to denoise the first frequency domain information, wherein, to denoise the first frequency domain information, the calculation module is configured to remove spectrum values, which correspond to frequency indexes of the denoising parameter, from the first frequency domain information, and the calculation module further configured to determine a heart rate index according to a denoised maximum spectrum peak value of the denoised first frequency domain information, and calculate a heart rate according to the heart rate index.

2. The heart rate detection module as claimed in claim 1, wherein the conversion module is configured to
convert the PPG signal to a frequency domain PPG signal,
generate the first frequency domain information according to the frequency domain PPG signal,
convert the acceleration signal to a frequency domain acceleration signal, and
generate the second frequency domain information according to the frequency domain acceleration signal.

3. The heart rate detection module as claimed in claim 1, wherein the first frequency index set and the second frequency index set have an identical number of frequency indexes.

4. The heart rate detection module as claimed in claim 1, wherein the
calculation module is further configured to calculate a half of the reference index and a double of the reference index,
wherein the denoising parameter further comprises at least one of the half of the reference index and the double of the reference index.

5. The heart rate detection module as claimed in claim 1, wherein the processing unit further comprises:
a heart rate monitoring module configured to record a variation tendency of heart rates corresponding to a plurality of the detection periods,
wherein the calculation module is further configured to estimate a heart rate according to the variation tendency.

6. The heart rate detection module as claimed in claim 1, wherein the heart rate detection module is integrated with a wearable device or a mobile device.

7. A heart rate detection method of a heart rate detection module, the heart rate detection module comprising a PPG measuring device, a motion sensor, a band pass filter and a processing unit, the heart rate detection method comprising:
detecting, by the PPG measuring device, a skin surface in a detection period to output a PPG signal;
outputting, by the motion sensor, an acceleration signal corresponding to the detection period;
filtering, by the band pass filter, the PPG signal and the acceleration signal;
receiving, by the processing unit, the PPG signal and the acceleration signal;
respectively converting, by the processing unit, the PPG signal and the acceleration signal to
first frequency domain information, which comprises a first frequency index set and a first spectrum value set associated with the first frequency index set, and
second frequency domain information, which comprises a second frequency index set and a second spectrum value set associated with the second frequency index set;
identifying, by the processing unit, a plurality of frequency indexes corresponding to a plurality of spectrum peak values in the first frequency domain information and the second frequency domain information;
determining, by the processing unit, a reference index as a denoising parameter according to a frequency index corresponding to a maximum spectrum peak value of the second frequency domain information to denoise the first frequency domain information, wherein denoising the first frequency domain information comprises removing spectrum values, which correspond to frequency indexes of the denoising parameter, from the first frequency domain information; and
determining, by the processing unit, a heart rate index according to a denoised maximum spectrum peak value of the denoised first frequency domain information, and calculating a heart rate according to the heart rate index.

8. The heart rate detection method as claimed in claim 7, wherein the respectively converting comprises:
converting, by the processing unit, the PPG signal to a frequency domain PPG signal and generating the first frequency domain information according to the frequency domain PPG signal; and
converting, by the processing unit, the acceleration signal to a frequency domain acceleration signal and generating the second frequency domain information according to the frequency domain acceleration signal.

9. The heart rate detection method as claimed in claim 7, further comprising:
calculating, by the processing unit, multiples of the reference index; and
taking, by the processing unit, the reference index and at least one of the multiples of the reference index as the denoising parameter.

10. The heart rate detection method as claimed in claim 7, wherein the calculating further comprises:
calculating, by the processing unit, the heart rate according to the heart rate index and frequency indexes adjacent to the heart rate index.

11. The heart rate detection module as claimed in claim 1, wherein a passband of the band pass filter is from 0.45 Hz to 4.5 Hz.

12. The heart rate detection method as claimed in claim 8, wherein the frequency domain PPG signal and the frequency domain acceleration signal are converted by Fast Fourier Transform or Discrete Fourier Transform.

13. The heart rate detection method as claimed in claim 7, wherein a passband of the band pass filter is from 0.45 Hz to 4.5 Hz.

* * * * *